United States Patent
Wing et al.

(10) Patent No.: US 7,896,884 B2
(45) Date of Patent: Mar. 1, 2011

(54) INTERBODY DISTRACTOR

(75) Inventors: Charles Wing, Center Valley, PA (US);
Keith Boyle, Whitehall, PA (US); Alex Vaccaro, Gladwyne, PA (US)

(73) Assignee: Aesculap, Inc., Center Valley, PA (US)

( * ) Notice: Subject to any disclaimer, the term of this patent is extended or adjusted under 35 U.S.C. 154(b) by 569 days.

(21) Appl. No.: 11/788,297

(22) Filed: Apr. 19, 2007

(65) Prior Publication Data

US 2008/0177275 A1 Jul. 24, 2008

Related U.S. Application Data

(60) Provisional application No. 60/872,126, filed on Dec. 1, 2006.

(51) Int. Cl.
*A61B 17/60* (2006.01)
*A61B 1/32* (2006.01)
(52) U.S. Cl. ............ 606/90; 606/99; 606/105; 606/914; 600/201
(58) Field of Classification Search .................... 606/99, 606/90, 105, 914; 600/201
See application file for complete search history.

(56) References Cited

U.S. PATENT DOCUMENTS

| | | | |
|---|---|---|---|
| 3,486,505 A | 12/1969 | Morrison | |
| 4,034,746 A | 7/1977 | Williams | |
| 4,997,432 A | 3/1991 | Keller | |
| 5,122,130 A | 6/1992 | Keller | |
| 5,314,477 A | 5/1994 | Marnay | |
| 5,571,109 A | 11/1996 | Bertagnoli | |
| 5,599,279 A | 2/1997 | Slotman et al. | |
| 5,697,889 A | 12/1997 | Slotman et al. | |
| 6,102,950 A | 8/2000 | Vaccaro | |
| 6,478,800 B1 * | 11/2002 | Fraser et al. | 606/99 |
| 6,755,841 B2 | 6/2004 | Fraser et al. | |
| 7,118,580 B1 * | 10/2006 | Beyersdorff et al. | 606/99 |

(Continued)

FOREIGN PATENT DOCUMENTS

DE 200 12 549 * 7/2000

(Continued)

OTHER PUBLICATIONS

McNamara et al., Potential of polyetheretherketone (PEEK) and carbon-fibre-reinforced PEEK in medical applications, 1987, Journal of Materials Science Letters 6, 188-190.*

(Continued)

*Primary Examiner* — Thomas C Barrett
*Assistant Examiner* — Sameh Boles
(74) *Attorney, Agent, or Firm* — RatnerPrestia

(57) ABSTRACT

A surgical instrument for insertion of an interbody fusion implant between adjacent vertebral bodies. The surgical instrument comprises a frame member, and a first and a second arm coupled to the frame member. Each arm includes a distal end region and a proximal end region, whereby the proximal end region of at least one arm is pivotably coupled to the frame member, and the distal end region of each arm defines a distractor plate. The distractor plate of each arm is configured to be positioned in direct contact with a vertebral body. A wedge is positioned between the first and second arms, and is configured to translate the interbody fusion implant along an axis between the proximal end region and the distal end region of the arms while adjusting a distance between the distractor plates of the arms via a rack and pinion.

17 Claims, 3 Drawing Sheets

U.S. PATENT DOCUMENTS

| | | |
|---|---|---|
| 2002/0068976 A1 | 6/2002 | Jackson |
| 2003/0236472 A1* | 12/2003 | Van Hoeck et al. ........... 600/587 |
| 2006/0241641 A1 | 10/2006 | Albans et al. |

FOREIGN PATENT DOCUMENTS

| | | |
|---|---|---|
| DE | 200 12 549 U1 | 7/2000 |
| DE | 20012549 U1 * | 10/2000 |

OTHER PUBLICATIONS

McNamara et al. Journal of Materials Science Letters 6 (1987) 188-190 (NPL).*

Medtronic Sofamor Danekl, Catalyst Anterior Instrument Set, www.sofamordanek.com, 2004 pp. 1-16.

* cited by examiner

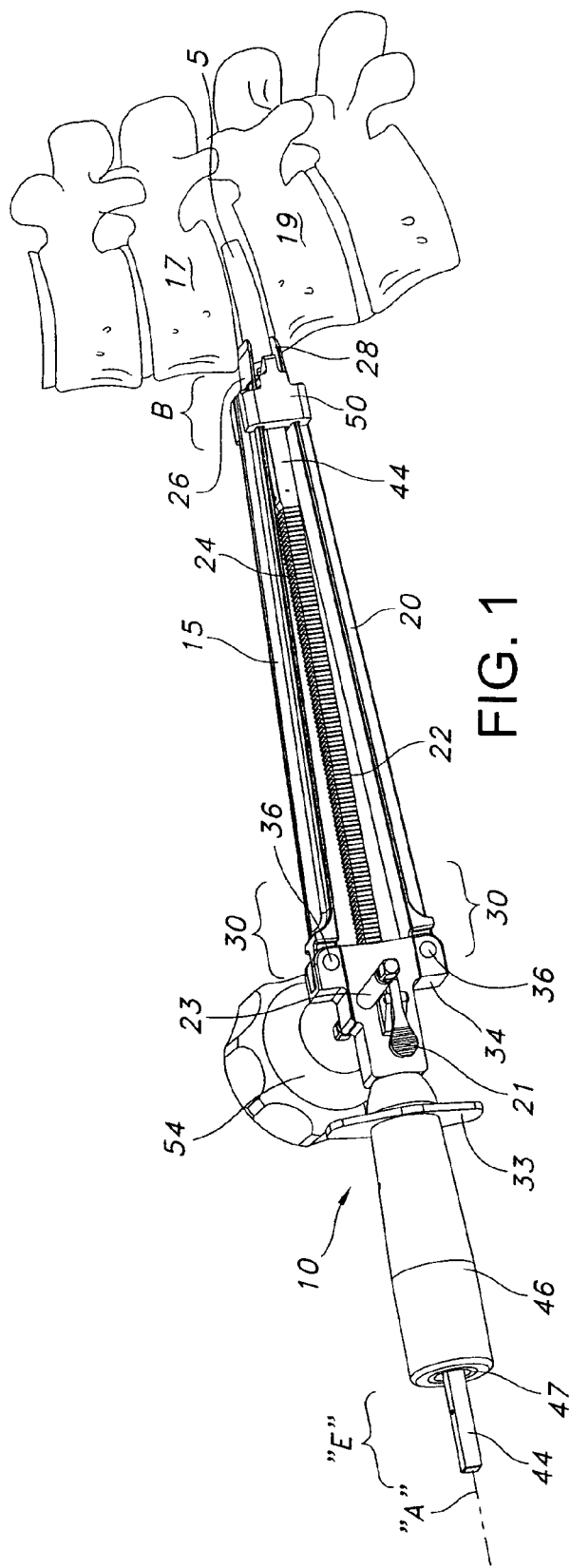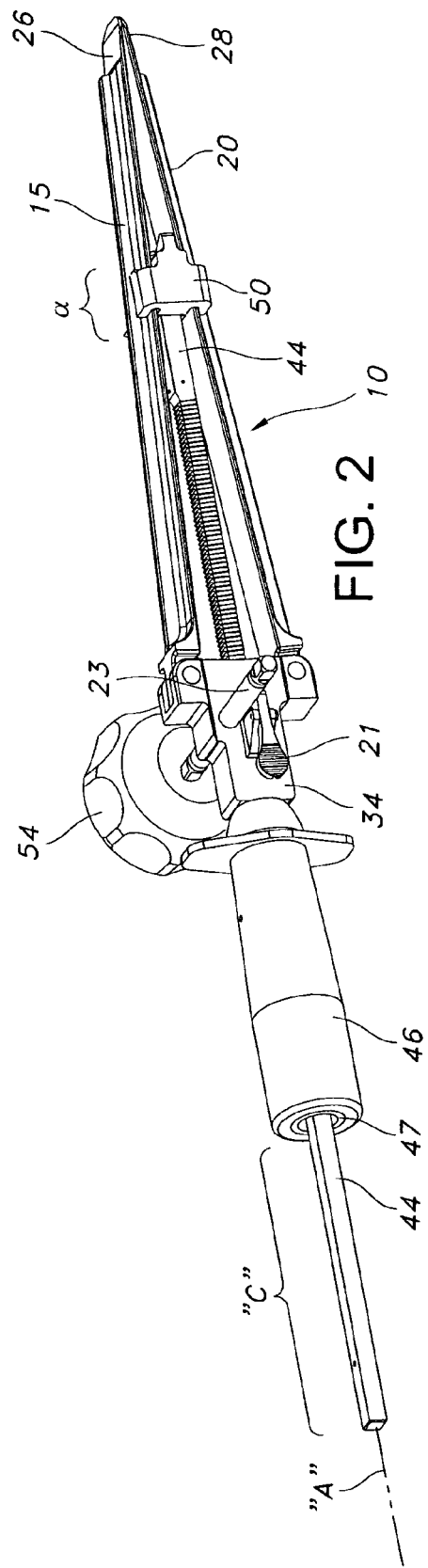

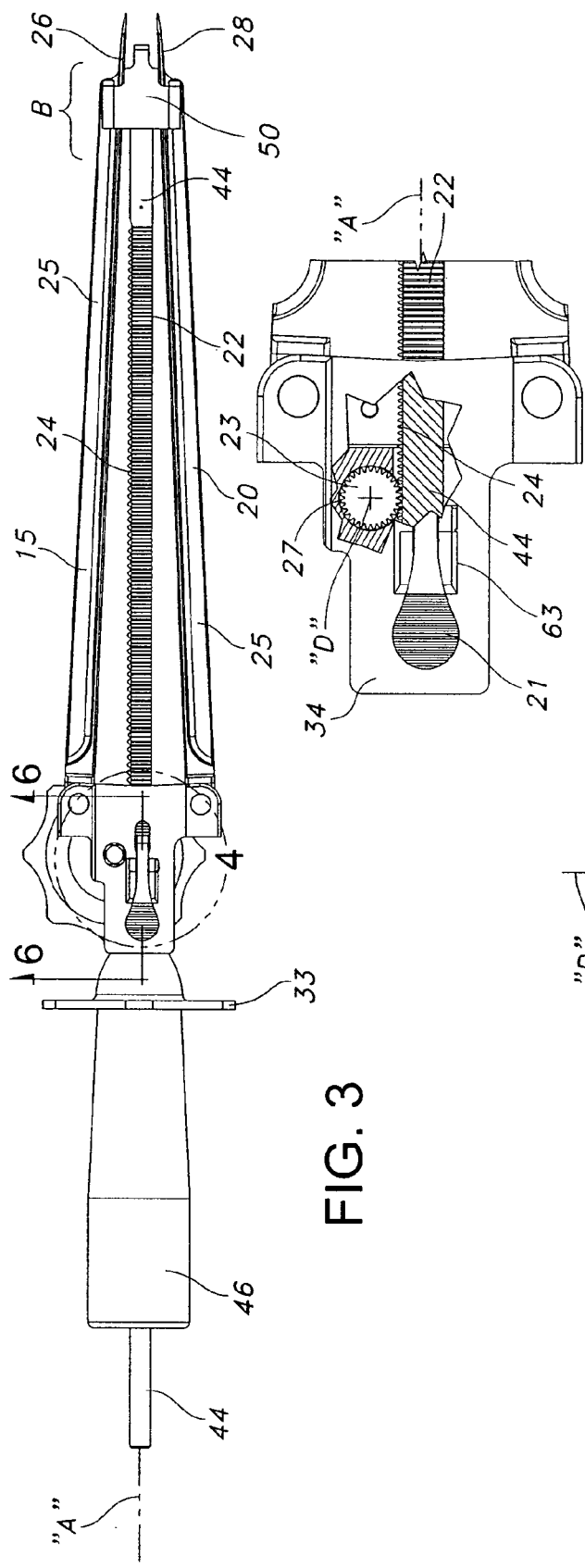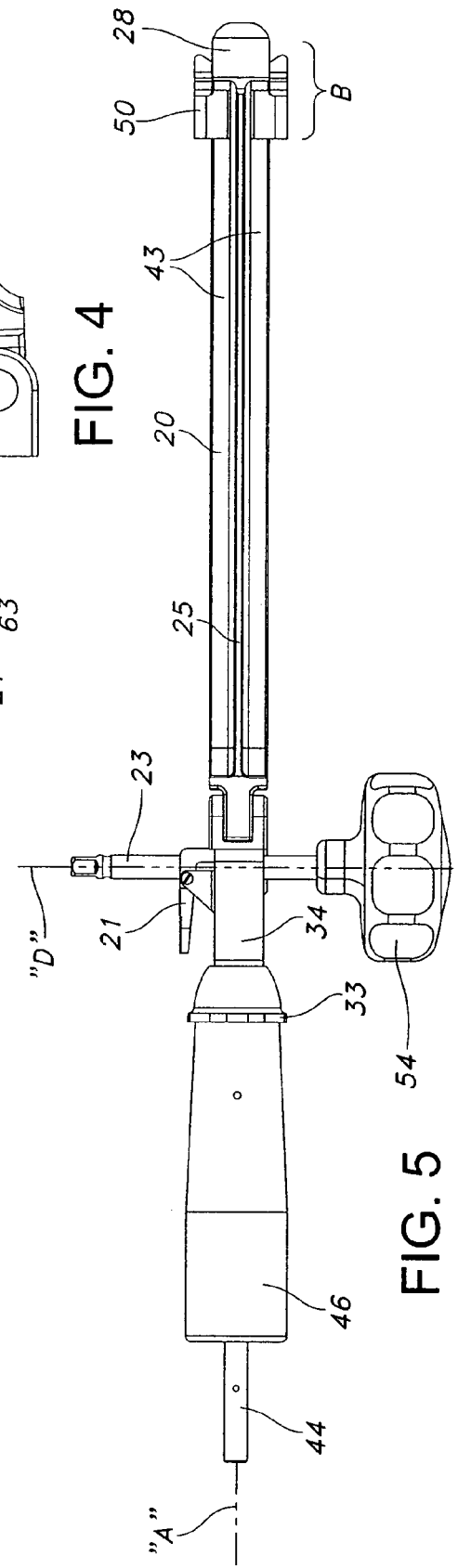

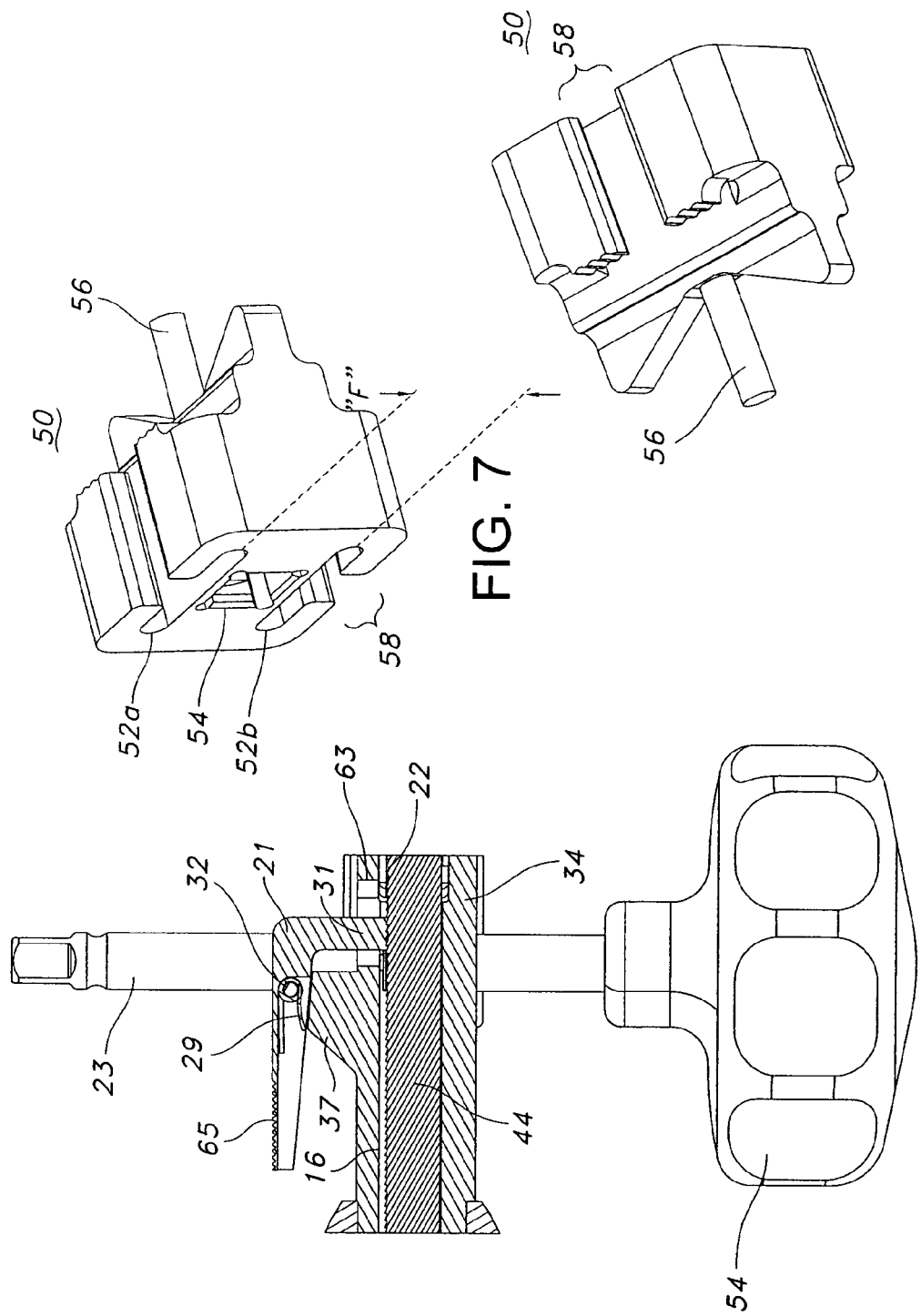

INTERBODY DISTRACTOR

CROSS REFERENCE TO RELATED APPLICATIONS

This application claims the benefit of the filing date of the provisional application entitled "ANTERIOR LUMBAR INTERBODY DISTRACTOR" filed Dec. 1, 2006 and assigned Ser. No. 60/872,126, the contents of which are incorporated herein by reference.

FIELD OF THE INVENTION

The present invention is directed to an apparatus and method for inserting an interbody fusion implant between adjacent vertebrae, and more particularly, to a distractor for use in anterior lumbar interbody fusion surgical techniques.

BACKGROUND OF THE INVENTION

A variety of interbody fusion implants exist for replacing damaged spinal disc segments of the human body. The interbody fusion implant is used to replace a deformed, injured or diseased natural intervertebral disc. An interbody fusion implant connects two adjacent vertebrae together, retains the vertebrae in the correct position, and limits their relative movement such that the adjacent vertebra and the implant fuse together.

There are various accepted procedures for installing intervertebral fusion implants or cages between adjacent lumbar vertebrae, such as, the posterior approach and the anterior approach. In the posterior approach, a surgeon makes an incision along the back of the patient. The surgeon moves the spinal muscles and nerve bundles, which are close to the surface of the back, to access the diseased disc. The diseased disc is replaced with an interbody fusion implant or cage. This is commonly referred to as a "posterior lumbar interbody fusion" (PLIF).

In the anterior approach (meaning from the front of the patient), a surgeon makes an incision in the abdomen of the patient. With the aide of one or more surgical instruments, the surgeon reaches through the chest cavity to access the damaged vertebral disc and replace it with the interbody fusion implant. This is commonly referred to as "anterior lumbar interbody fusion" (ALIF). The invention disclosed herein is particularly useful for ALIF procedures, but could also be useful for a PLIF procedure with minor modifications.

An ALIF distractor is shown and described in U.S. Pat. No. 7,118,580 to Beyersdorff et al. This reference discloses an ALIF distractor for installing a three-piece artificial disc between adjacent vertebral bodies. The three-piece artificial disc comprises an upper part for placement against a first vertebral body, a lower part for placement against an adjacent lower vertebrae, and a pivot element that can be inserted between the upper and lower parts. The insertion instrument comprises two elongated arms, disposed side by side and pivotably supported relative to one another. A retention pin is positioned at the end of each elongated arm, whereby the retention pins are inserted into bores provided in the upper part and the lower part of the intervertebral implant. A thrust guide is positioned between the arms of the insertion instrument for inserting the pivot element between the upper part and the lower part of the artificial disc.

In practice, the upper and lower parts of the artificial disc are first installed on adjacent vertebrae. Thereafter, the thrust guide is slid between the arms of the insertion instrument, spreading apart the elongated arms and the adjacent vertebrae. The pivot element of the artificial disc is pushed between the upper part and the lower part of the artificial disc by the thrust guide. After the pivot element is set in place, the thrust guide is retracted thereby contracting the arms and closing the large gap between the adjacent vertebrae. The pivot element is then captivated between the upper part and the lower part of the artificial disc.

The ALIF distractor of '580 is tailored for use with a three-piece intervertebral disc implant. Because other types of disc implants and fusion implants exist, such as a one piece fusion implant, there remains a need for alternative ALIF distractors. Furthermore, despite existing ALIF distractors, there remains a need to provide an ALIF distractor to facilitate the proper and convenient insertion of an fusion implant between adjacent vertebral bodies using the ALIF surgical technique while minimizing the risk of injury to the patient.

SUMMARY OF THE INVENTION

According to one aspect of the invention, a surgical instrument for insertion of an interbody fusion implant between adjacent vertebral bodies is provided. The surgical instrument comprises a frame member, and two arms coupled to the frame member. Each arm includes a distal end region and a proximal end region, whereby the proximal end region of at least one arm is pivotably coupled to the frame member, and the distal end region of each arm defines a distractor plate. The distractor plate of each arm is configured to be positioned in direct contact with a vertebral body. A wedge is configured to translate the interbody fusion implant along an axis between the proximal end region and the distal end region of the arms while adjusting a distance between the distractor plates of the arms. A rack is coupled to the wedge and is slideably positioned at least partially through the frame member along the axis. A pinion is positioned at least partially through the frame member for engagement with the rack, wherein rotation of the pinion translates the rack along the axis.

Specifically, translation of the wedge from the proximal end region of the arms to the distal end region of the arms translates the interbody fusion implant toward the adjacent vertebrae while distracting the adjacent vertebral bodies for placement of the interbody fusion implant between the distracted adjacent vertebrae.

According to another aspect of the invention, a method of inserting an interbody fusion implant between two adjacent vertebral bodies using a surgical instrument is provided. The surgical instrument comprises a pair of arms each defining a distractor plate for contacting a vertebrae, and a wedge positioned at least partially between the arms for spreading the distractor plates while translating the interbody fusion implant relative to the vertebral bodies. The method comprises the step of positioning the extractor plate of each arm on a surface of a vertebral body. The wedge is translated along the arms to spread the arms apart, thereby distracting the vertebral bodies, and urging the interbody fusion implant between the distracted vertebral bodies.

BRIEF DESCRIPTION OF THE DRAWINGS

The invention is best understood from the following detailed description when read in connection with the accompanying drawings. It is emphasized that, according to common practice, the various features of the drawings are not to scale. Included in the drawings are the following figures:

FIG. 1 is a perspective view of an exemplary ALIF distractor according to an embodiment of the present invention shown mounting an interbody fusion implant between spaced apart vertebrae;

FIG. 2 is a perspective view of the exemplary distractor of FIG. 1, wherein the wedge of the distractor is positioned at a proximal location;

FIG. 3 is an elevation view of the exemplary distractor of FIG. 1, wherein the wedge of the distractor is positioned at a distal location;

FIG. 4 is a partial cut-away enlarged detail view of the exemplary distractor of FIG. 3, illustrating the engagement between the rack and pinion gear;

FIG. 5 is a top plan view of the exemplary distractor of FIG. 3;

FIG. 6 is a cross-sectional view of the distractor of FIG. 3 taken along the lines 6-6;

FIG. 7 is a perspective view from the top left corner of the wedge of FIG. 1; and FIG. 8 is a perspective view from the top right corner of the wedge of FIG. 1.

DETAILED DESCRIPTION OF THE INVENTION

The invention will next be illustrated with reference to the figures. Such figures are intended to be illustrative rather than limiting and are included herewith to facilitate explanation of the present invention.

FIGS. 1-6 illustrate various views of an exemplary embodiment of an ALIF distractor 10, according to aspects of the present invention. Although only one exemplary embodiment of the ALIF distractor 10 is shown in the figures, numerous variations of that exemplary embodiment are described hereinafter.

In FIG. 1, the ALIF distractor 10 is shown in the course of installing an interbody fusion implant 5 into an intervertebral space defined between two adjacent vertebral bodies 17 and 19 of a vertebral column. Briefly, in practice, after a damaged disc is extracted, the ALIF distractor 10 is employed to install an interbody fusion implant 5 into the empty intervertebral space. The ALIF distractor 10 is generally configured to spread the adjacent vertebral bodies 17 and 19 apart far enough to insert the implant 5 into the intervertebral space. After inserting the fusion implant 5 between the adjacent vertebrae, the ALIF distractor 10 is removed from the intervertebral space, permitting the vertebral bodies 17 and 19 to return to their natural position. The fusion implant 5 is maintained in a state of compression between the vertebrae.

Referring now to FIGS. 1, 3 and 5, perspective, front and top plan views of distractor 10 are shown. The ALIF distractor 10 generally comprises a central frame member 34, opposing arms 15 and 20 pivotably coupled to the right side of the frame member 34, a handle 46 mounted to the left side of the frame member 34, and a rack 44 slideably carried through channels provided in the frame member 34 and the handle 46. The terms 'proximal' and 'distal' used throughout are defined relative to the frame member 34 of the distractor 10.

The first arm 15 and the second arm 20 are each pivotably coupled to the frame member 34 by a pin 36, or any other apparatus for facilitating rotational motion. Although both arms are shown pivotably coupled to the frame 34, it should be understood that only one arm may be pivotably coupled to the frame 34 to provide the same or similar functionality. The first arm 15 and the second arm 20 each have a proximal end region 30, i.e., the end regions 30 are proximal to the frame member 34. The proximal end regions 30 are each pivotably coupled to the frame member 34 about a pin 36, as mentioned above. According to an exemplary embodiment, the overall length of each arm may be about 150 to about 400 mm, for example.

Each arm 15 and 20 has a "T"-shaped cross section. The "T" shape of each arm comprises a substantially flat portion 43 (see FIG. 5) and a spine 25 (see FIG. 3) extending from the top side of the flat portion 43. The spine 25 confers rigidity and strength to the arms 15 and 20 to limit bending and twisting of the arms during an ALIF procedure. The underside of each flat portion 43 is defined by a smooth and flat surface, such that a wedge 50 may translate along the arms 15 and 20 without interruption, as described in greater detail with reference to FIGS. 7 and 8.

A pair of distractor plates 26 and 28 are defined on the distal end portion of each arm 15 and 20, respectively. As best shown in FIG. 1, each distractor plate 26 and 28 directly contacts a vertebrae 17 and 19, respectively. The distractor plates 26, 28 are sized for insertion between adjacent vertebral bodies. The edges of the distractor plates 26, 28 may be flat, beveled or radiused, for insertion into an intervertebral space. Furthermore, the distractor plates 26 and 28 may also be curved or angled in a superior or inferior direction (i.e., orthogonal to axes "A" and "D") for insertion into an intervertebral space. The length of each distractor plate 26, 28 corresponds to the insertion depth of the interbody fusion implant. According to one embodiment, the length of each distractor plate 26, 28 is about 5 mm to about 15 mm. The distractor plates 26 and 28 may be integrally formed with the arms 15 and 20, or, alternatively, the distractor plates may be separate components mounted onto the distal end regions of the arms. In use, the distractor plates 26 and 28 of the arms 15 and 20 are positioned to directly contact the adjacent vertebrae 17 and 19.

The cannulated handle 46 is provided for grasping the distractor 10 during an ALIF procedure. The cannulated handle 46 is mounted to the left side of the frame member 34, by a fastener, weld, or any other mounting method known to those skilled in the art. In this embodiment, the handle 46 is defined by a long cylindrical body, optionally including a tacky or serrated outer surface for enhanced user dexterity. A flange 33 is also provided at the proximal end of the handle 46 (i.e., proximal to the frame member 34) for enhanced user dexterity. A bore 47 is disposed through the entire length of the handle 46, through which the rack 44 is slideably carried.

The rack 44 is slideably carried within a passage 16 (see FIG. 6) defined within the frame member 34, and the bore 47 of the handle 46. The rack 44 translates along the longitudinal axis "A" of the ALIF distractor 10. According to this exemplary embodiment, the rack 44 is a bar having a square-cross sectional shape. However, those skilled in the art will recognize that the rack 44 may be a long bar, rod, tube, or pipe having a square, circular or rectangular cross-section.

The rack 44 includes two sets of gear teeth 22 and 24. The first set of gear teeth 22 are disposed along a portion of the front side of the rack 44, as best shown in FIGS. 1 and 3. The second set of gear teeth 24 are disposed along a portion of the top side of the rack 44, as best shown in FIG. 1. The gear teeth 22 and 24 are independently utilized to finely control the translation of the rack 44 along axis "A," as described in greater detail below. The rack 44 is shown in a fully extended position along axis "A" in FIG. 1, as indicated by the dimension "E," and the rack 44 is shown in a retracted position in FIG. 2, as indicated by dimension "C." In the fully extended position in use, the constrained end of the rack 44 is in close proximity to the spinal column.

Referring now to FIGS. 1 & 2, a wedge 50 is mounted to the constrained end of the rack 44. Accordingly, the wedge 50 translates with the rack 44 along axis "A." In addition to translating along axis "A," the wedge 50 cooperates with the arms 15 and 20, such that as the wedge 50 translates along axis "A", the wedge 50 pivots the arms 15 and 20 about their respective pins 36. More particularly, as the wedge 50 is translated from a proximal position "a" (see FIG. 2) to a distal position "B" (see FIG. 1), the wedge 50 spreads the distractor plates 26 and 28 of the arms 15 and 20 apart. Conversely, as the wedge 50 is translated from the distal position "B" (see FIG. 1) to the proximal position "a" (see FIG. 2), the wedge 50 draws the distractor plates 26 and 28 of the arms 15 and 20 together, as best shown in FIG. 2. The wedge 50 is mounted to the constrained end of the rack 44, by a fastener, split pin, or other apparatus (not shown). The interbody fusion implant 5 is releasably coupled to the wedge 50, such that the interbody fusion implant may be released from the wedge 50 after it is inserted between the adjacent vertebrae 17 and 19. Further details of the wedge 50 are described in greater detail with reference to FIGS. 7 and 8.

Referring now to FIGS. 3 and 4, a pinion 23 is rotatably positioned through a hole disposed in the central frame 34 of the distractor 10. A pinion gear 27 projects from the outer circumference of the pinion 23. The pinion gears 27 extend along the length-wise portion of the pinion 23 that is positioned within the central frame member 34. The pinion 23 is configured to rotate about axis of rotation "D" in either a clockwise or a counter-clockwise direction.

In FIG. 4, a portion of the central frame member 34 is cut-away to reveal the pinion gears 27 of the pinion 23. As best shown in the cut-away view of FIG. 4, the pinion gears 27 of the pinion 23 are positioned for engagement with the gear teeth 24 of the rack 44, such that rotation of the pinion 23 about axis of rotation "D" induces translation of the rack 44 (and wedge 50) along axis "A." Conversely, translation of the rack 44 (and wedge 50) along axis "A" induces rotation of the pinion 23 about axis of rotation "D."

A knob 54 is mounted to one end of the pinion 23 to facilitate manual rotation of the pinion 23 about axis of rotation "D." According to one embodiment, rotation of the knob 54 in a clockwise direction translates the wedge 50 in a forward direction toward the distal position "B," and rotation of the knob 54 in a counter-clockwise direction translates wedge 50 along axis "A" in a backward direction toward a proximal position "a," or vice versa, depending upon end user requirements.

Referring now to FIG. 6, a cross section of the frame member 34 taken along the lines 6-6 of FIG. 5 is shown. The distractor 10 includes a spring loaded catch 21 for preventing backwards translation (i.e., towards the proximal position "a") of the rack 44 through the rack channel 16, and unconstrained rotation of pinion 23. The catch 21 is pivotably mounted to the frame member 34 about a pin 32. The pin 32 passes through holes (not shown) disposed on opposite sides of the catch 21 and mounts to opposing flanges 37 (one shown in FIG. 6) extending from the front surface of the frame member 34, such that the catch 21 is pivotably mounted to the frame member 34 about the pin 32. A coil spring 29 is positioned over the pin 32 to bear on the catch 21 and the flange 37 of the frame member 34. The force exerted by the spring 29 biases the catch 21 into engagement with the rack 44, as shown in FIG. 6.

The catch 21 includes a serrated end 31 that is positioned through a slot 63 provided on the front surface of the frame member 34 (slot 63 also shown in FIG. 4). The serrated end 31 of the catch 21 engages the gear teeth 22 of the rack 44, by virtue of the force exerted by the spring 29. Once the serrated end 31 of the catch 21 frictionally engages the gear teeth 22 of the rack 44, by virtue of the force exerted by the spring 29, the rack 44 is limited from translating in the forward direction along axis "A."

Specifically each tooth of the serrated end 31 and the gear teeth 22 are sloped at right angles, as shown in FIG. 6, such that the teeth 31 and 22 may slide past each other in one direction, but bear on each other in the opposite direction. Accordingly, once the catch 21 bears on the rack 44, the rack 44 is prohibited from translating along axis "A" in the backwards direction (i.e., toward the proximal position "α"), yet the rack 44 may translate in the forward direction (i.e., toward the distal position "B"). It should be understood, however, that the pressure exerted onto the rack 44 by the spring loaded catch 21 limits the rack 44 from "freely" translating in the forward direction. More particularly, the rack 44 translates in the forward direction only by rotating the knob 54 or impacting the free end of the rack 44 with a mallet or other instrument. Thus, the catch 21 is configured to both prevent the rack 44 from translating backwards, and prevent free translation of the rack 44 in the forward direction.

Manually depressing the free end 65 of the spring loaded catch 21 disengages the catch 21 from the rack 44. Thereafter, the rack 44 may freely translate through rack channel 16 in both the forward and backwards direction without interference. The rack 44 may then be quickly removed from the distractor 10. The rack 44 is disengageable from the wedge 50, such that the rack 44 may be completely removed from the distractor 10, if so desired, as described in greater detail with reference to FIGS. 7 and 8.

Referring now to FIGS. 7 and 8, perspective views of the wedge 50 are shown. The wedge 50 is a substantially block-like object including two slots 52a and 52b for slideably carrying the arms 15 and 20. An opening 54 is provided in the wedge 50 for receiving the distal end of the rack 44, and a split pin 56 is positioned on an opposing side of the wedge for releasably carrying the interbody fusion implant 5.

The slots 52a and 52b are sized to retain the arms 15 and 20 of the distractor 10 therewithin, while the wedge 50 translates over the arms 15 and 20 along axis "A." The length and width of each slot 52a and 52b is slightly greater than the length and width of the flat portions 43 of each arm, to permit the wedge 50 to freely translate over the arms. Each slot 52a and 52b includes an opening 58 to accommodate the spine 25 of each arm 15 and 20.

The wedge 50 includes an opening 54 for releasable attachment to the constrained end of the rack 44, such that the rack 44 may be removed from the distractor 10 if so desired. The wedge 50 may be releasably attached to the rack 44 by any means known in the art, such as a pin, split pin, fastener, friction, screw threads, and so forth. Although the rack 44 may be removed from the wedge 50, it should be understood that the wedge 50 remains captivated to the first and second arms 15 and 20 thereby preventing the first and second arms 15 and 20 from separating uncontrollably upon removal of the rack 44.

According to the exemplary embodiment shown in FIGS. 7 and 8, a split pin 56 is mounted to the end of the wedge 50. The split pin 56 extends through a hole (not shown) formed in the wedge 50. Alternatively, the pin 56 may be integrally formed with the wedge 50. Although not shown, the interbody fusion implant 5 includes a hole for receiving the split pin 56. The split pin 56 and the hole of the interbody fusion implant are sized such that the frictional engagement therebetween is large enough to retain the implant during an insertion procedure, yet small enough to permit disengagement of the interbody fusion implant from the wedge 50 once the implant is installed between adjacent vertebrae.

The vertical distance "F" separating the slots 52a and 52b is sized such that when the wedge 50 is at its distal position "B," the intervertebral space between the adjacent vertebrae created by the distractor plates 26 and 28 is greater than the height of the interbody fusion implant 5, so that the interbody fusion implant 5 may be installed within the intervertebral space. Because interbody fusion implants 5 vary in height, an assortment of wedges having different vertical heights "F" may be offered to compliment the various interbody fusion implants. According to one exemplary embodiment, the wedges are available in millimeter increments from 9 mm in height to 22 mm in height, and are selected according to the anatomical situation and the degree of distraction required by the surgical technique employed. Thus, the distractor 10 may be packaged in a kit with a plurality of wedges 50 of varying height.

The wedge 50 may be formed from any suitable surgical material. According to an exemplary embodiment, wedge 50 is formed from a plastic material that is sufficiently robust to withstand the loads applied to it. The exterior surfaces of the wedge 50 may have a low coefficient of friction to enable the wedge 50 to slide along the exterior surfaces of the arms 15 and 20. Suitable plastic materials include polyketones, such as polyetheretherketones (PEEK). PEEK is a thermoplastic material having a Young's modulus of about 3.6 GPa and a tensile strength of about 170 MPa. PEEK is partially crystalline, and has a glass transition temperature of about 143° C., a melting temperature of about 334° C., and is highly resistant to thermal degradation and mechanical stresses.

An exemplary method of using a distractor 10 of the present invention includes the step of coupling the interbody fusion implant 5 to the pin 56 extending from the wedge 50. Depending upon the initial position of the wedge 50, knob 54 may be rotated until the wedge 50 is located at the proximal position a, as shown in FIG. 2. The distractor plates 26 and 28 are then inserted between the desired vertebrae where an interbody fusion implant 5 is to be inserted, as shown in FIG. 1. The knob 54 of the distractor is rotated, thereby advancing the rack 44 and distracting the adjacent vertebrae, until the wedge 50 contacts the vertebral bone 17 and/or 19 and applies a force against the vertebral bone. Further advancement of the wedge 50 (by rotation of the knob 54) towards the distal position "B", as the wedge 50 pushes against the vertebral bone, causes the distractor plates 26 and 28 to retract from the intervertebral space. Thus, the distractor 26 and 28 plates retract from the vertebral space with respect to the wedge 50, which remains pressed against the vertebrae. Once the distractor plates 26 and 28 are completely retracted from the intervertebral space, the pin 56 of the wedge 50 may be detached from the interbody fusion implant, leaving the implant 5 positioned between the adjacent vertebrae. The compressive forces applied to the interbody fusion implant 5 by the adjacent vertebrae are sufficient to retain the interbody implant between the vertebrae, such that the implant will not slip out of the intervertebral space while removing the pin 56 of the distractor 10 from the implant 5.

After installing the fusion implant 5 between the adjacent vertebrae, the surgeon may perform a number of additional steps to adjust the position of the interbody fusion implant 5 within the intervertebral space. According to one exemplary use of the distractor 10, the rack 44 is replaced with an impacting rack (not shown), while the wedge 50 remains attached to the fusion implant and coupled to the arms 15 and 20. The impacting rack is similar to the rack 44, however the impacting rack may include a large landing area on its free end for absorbing the impact force of a mallet. The impacting rack also may not include teeth, such as teeth 22 and 24 shown in FIG. 1, so that the impacting rack may slide freely through the channel 16 of the frame 34 and bore 47 of the handle 46.

To install the impacting rack, the rack 44 is first disengaged from the wedge 50. As described above, the rack 44 may be releasably attached to the wedge 50 by a spring loaded pin, fastener, threads, or any other means of releasable attachment known in the art. The free end 65 of the catch 21 is then depressed, to disengage the serrated end 31 of the catch 21 from the teeth 22 of the rack 44. The rack 44 may then be removed from the distractor 10 by pulling it through the frame 34 and cannulated handle 46 and out of the distractor 10 (while the wedge 50 remains attached to the interbody fusion implant). The impacting rack (not shown) is inserted through the bore 47 formed in the cannulated handle 46 and the rack channel 16 of the frame member 34 and releasably fastened to the wedge 50. Once the impacting rack is inserted into the distractor 10, a surgeon strikes the impacting rack to set the interbody fusion implant into its final position. Because the impacting rack does not have teeth to engage the pinion gear 27, the rack moves freely through the channel 16 of the frame member 34 when it is impacted by the mallet, without damaging gears.

According to an exemplary embodiment, distractor 10 may be used for direct anterior approach spinal surgery (typically for placing implants between vertebrae L5/S1) or for use in antero-lateral approach spinal surgery (typically for placing implants between lumbar vertebrae L4/L5, L3/L4, etc.). For the antero-lateral approach, the disc space is approached at an angle of about 45 degrees with respect to patient's abdomen. For the antero-lateral approach, the disc space is approached obliquely. Furthermore, according to another exemplary embodiment, distractor 10 may be used for posterior approach spinal surgery (i.e., PLIF procedures, as described above) with minor modifications. Specifically, the maximum width of a PLIF distractor would be about 7 mm to about 8 mm, for example. It should be understood by one skilled in the art that the distractor 10 may be modified to conform to various regions of the spine, or various discectomy, fusion, and laminectomy procedures.

Although exemplary embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A surgical instrument for insertion of an interbody fusion implant between adjacent vertebral bodies, comprising: a frame member having a proximal end and a distal end; a first arm and a second arm coupled to the distal end of the frame member, each arm having a distal end region and a proximal end region, the proximal end region of at least one arm being pivotably coupled to the frame member, and the distal end region of each arm defining a distractor plate; said distractor plate of each arm being configured to be positioned in direct contact with a vertebral body; a handle coupled to the proximal end of the frame member; a wedge positioned between said first and second arms, said wedge being configured to translate the interbody fusion implant along an axis between said proximal end region and said distal end region of said arms while adjusting a distance between said distractor plates of said arms, wherein the interbody fusion implant is releasably coupled to said wedge; a rack coupled to said wedge and being slideably positioned at least partially through said frame member and said handle, the rack comprising a first side with a first set of teeth and a second side with a second set of teeth; a pinion positioned at least partially through said frame member for engaging said first set of teeth, wherein rotation of said pinion translates said rack and said wedge along said axis when the pinion engages the first set of teeth; and a catch for selective engagement with the second set of teeth, the second set of teeth shaped so that when engaged with the catch, the second set of teeth allows translation of the rack relative to the frame member in one direction when the pinion is rotated in a first direction, but Prevents translation of the rack relative to the frame member in the opposite direction when the pinion is rotated in a second direction, wherein translation of said wedge from said proximal end region of said arms toward said distal end region of said arms translates the interbody fusion implant toward the adjacent vertebrae while distracting the adjacent vertebral bodies for placement of the interbody fusion implant between the distracted adjacent vertebrae.

2. The surgical instrument of claim 1 wherein said frame member defines a channel for slideably carrying said rack.

3. The surgical instrument of claim 1, said rack being releasably coupled to said wedge.

4. The surgical instrument of claim 1, wherein the first set of teeth on the rack comprise a plurality of gear teeth for engagement with a plurality of gear teeth defined on said pinion.

5. The surgical instrument of claim 1 further comprising a knob coupled to said pinion for rotating said pinion.

6. The surgical instrument of claim 1, said wedge defining at least one slot, through which said first arm or said second arm is slidingly captivated.

7. The surgical instrument of claim 1 wherein the interbody fusion implant is releasably coupled to said wedge by a split pin positioned between the interbody fusion implant and said wedge.

8. The surgical instrument of claim 1, wherein at least one distractor plate includes a non planar surface for contacting a vertebra.

9. The surgical instrument of claim 1 wherein said wedge is composed of poly(etheretherketone) (PEEK).

10. A kit comprising the surgical instrument of claim 1 and a plurality of wedges, wherein a dimension of at least one each wedge varies.

11. A surgical instrument for insertion of an interbody fusion implant between adjacent vertebral bodies, comprising: a frame member having a proximal end and a distal end; a first arm and a second arm coupled to the distal end of the frame member, each arm having a distal end region and a proximal end region, the proximal end region of at least one arm being pivotably coupled to the frame member, and the distal end region of each arm defining a distractor plate; said distractor plate of each arm being configured to be positioned in direct contact with a vertebral body; a handle coupled to the proximal end of the frame member; a wedge positioned between said first and second arms, said wedge being configured to translate the interbody fusion implant along an axis between said proximal end region and said distal end region of said arms while adjusting a distance between said distractor plates of said arms; a rack coupled to said wedge and being slideably positioned at least partially through said frame member and said handle, the rack comprising a first side with a first set of teeth and a second side with a second set of teeth; a pinion positioned at least partially through said frame member for engaging said first set of teeth, wherein rotation of said pinion translates said rack and said wedge along said axis when the pinion engages the first set of teeth; and a catch configured for selective engagement with the second set of teeth to limit translation of said rack relative to said distractor plate in at least one direction when said catch is engaged with said rack, wherein translation of said wedge from said proximal end region of said arms toward said distal end region of said arms translates the interbody fusion implant toward the adjacent vertebrae while distracting the adjacent vertebral bodies for placement of the interbody fusion implant between the distracted adjacent vertebrae.

12. The surgical instrument of claim 11 wherein the catch comprises a serrated end positioned for selective engagement with gear teeth extending from a surface of the rack.

13. The surgical instrument of claim 12 wherein engagement between said catch and said rack prevents translation of said rack in a direction along said axis.

14. The surgical instrument of claim 13 wherein engagement between said catch and said rack limits free translation of said rack in an opposite direction along said axis.

15. The surgical instrument of claim 12 wherein said catch is spring loaded and biased to a position where said rack is engaged with said catch.

16. A method of inserting an interbody fusion implant between two adjacent vertebral bodies using a surgical instrument comprising a frame having a proximal end and a distal end, a pair of arms coupled to the distal end of the frame, each arm defining a distractor plate for contacting one of said two adjacent vertebral bodies, a handle coupled to the proximal end of the frame, a rack translatable along an axis defined between the arms and being slideably positioned at least partially through said frame and said handle, a pinion engageable with the rack to induce translation of the rack along the axis and a wedge coupled to the rack for translating the interbody fusion implant and spreading the arms, said method comprising the steps of:
  positioning the extractor plate of each arm on a surface of one of said two adjacent vertebral bodies;
  rotating the pinion to engage a first set of teeth on a first side of the rack, translate the rack and the wedge, and spread the arms apart to distract the vertebral bodies, thereby urging the interbody fusion implant between the distracted vertebral bodies;
  engaging a catch with a second set of teeth on a second side of the rack, wherein the catch is configured to limit translation of the rack along the axis in one direction and permit translation of the rack in an opposite direction.

17. The method of claim 16, further compromising the steps of disengaging the catch from the rack, removing the rack from the surgical instrument, and inserting an impacting rack into the distractor.

* * * * *